United States Patent [19]

Walliczek

[11] 4,243,656

[45] Jan. 6, 1981

[54] BIOSYNTHETIC POLYMERIC COMPOSITIONS

[76] Inventor: Erwin G. Walliczek, 13 Biarritz Ave., Beaumaris 3193, Victoria, Australia

[21] Appl. No.: 37,474

[22] Filed: May 9, 1979

[30] Foreign Application Priority Data

May 19, 1978 [AU] Australia ............................... PD4440
Oct. 30, 1978 [AU] Australia ............................... PD6580

[51] Int. Cl.³ ....................... A61K 31/78; A61L 15/00
[52] U.S. Cl. ......................................... 424/28; 424/81
[58] Field of Search .................................. 424/28, 81

[56] References Cited

U.S. PATENT DOCUMENTS 3,579,628  5/1971  Gander et al. ......................... 424/28
3,963,685  6/1976  Abrahams ............................... 424/81

OTHER PUBLICATIONS

Chemical Abstracts, vol. 84, (1976), p. 91928g.
Fein, "Modern Drug Encyclopedia", 8th Ed., (1961), pp. 524–525.

Primary Examiner—Shep K. Rose
Attorney, Agent, or Firm—Trexler, Wolters, Bushnell & Fosse, Ltd.

[57] ABSTRACT

Biosynthetic polymeric compositions containing polyacrylate polymer, humectants such as glycerol, proteinaceous material such as gelatin, and water are prepared. The compositions are suitable for treatment of burns or other wounds and may be applied directly or in the form of a prepared film. The film may include a strengthening nylon mesh matrix.

7 Claims, No Drawings

BIOSYNTHETIC POLYMERIC COMPOSITIONS

This invention relates to biosynthetic polymeric films suitable for use in the treatment of burns, lacerations and surgical or other wounds and particularly but not exclusively to biosynthetic polymeric films suitable for use in the treatment of first and second degree burns.

Previously burns have been treated by covering the affected area with Tulle Gras dressings more recently with split thickness pig skin dressings.

Tulle gras dressings have the disadvantage of adhering to the area being treated due to the passage of blood and other body fluids through the dressing.

The more recent split thickness pig skin dressings have the disadvantage that they are expensive to prepare by virtue of the labour necessary for the preparation of such dressings; that they must be stored at low temperatures (e.g. $-150°$ C.); that they do not keep for extended periods; and that it is difficult to prepare such dressings to cover a large area with a single dressing.

It is an object of the present invention to overcome these disadvantages.

I have now found that certain acrylic copolymers together with certain humectants and proteinaceous material additives form biosynthetic polymeric films which are cheap to prepare, do not adhere to the area being treated, prevent ingress of bacteria whilst being air and moisture permeable and can be prepared in any desired sizes. The biosynthetic polymeric films of the invention can be sealed in individual packages and sterilized in for example by ethylene oxide treatment or by gamma irradiation.

The invention therefore provides a biosynthetic polymeric composition which includes:

an acrylic polymer in an amount of at least 10% by weight on a dry weight basis;

a humectant in an amount of from 2% to 30% by weight;

a proteinaceous material in an amount of from 0.5% to 15% by weight; and water in a total amount of from 30% to 70% by weight.

The combined weight of the humectant and the proteinaceous material is preferably not less than 8% more preferably not less than 10%.

The humectant is selected from glycerol, polyethylene glycol or propyl 1,2 diol and is preferably glycerol.

The proteinaceous material is selected from gelatin, or human, bovine or egg albumin.

The acrylic polymer preferably contains from 50 to 500 monomers per polymer and ideally from 100 to 300 monomers per polymer.

The acrylic polymer is preferably present in an amount of from 10% to 40% and ideally in an amount of from 12% to 33% on a dry weight basis.

The humectant glycerol is preferably present in an amount of from 3.7% to 28.4% and ideally from 5 to 15% by weight.

The proteinaceous material, gelatin is preferably present in an amount of from 5% to 14% and ideally from 5% to 10% by weight.

The combined humectant and proteinaceous material is preferably 10% by weight minimum and ideally 15% by weight minimum.

The biosynthetic polymeric composition of the invention may be in the form of a liquid emulsion or a polymerised film of thickness 0.05 to 0.4 mm.

The polymerised film of the invention preferably includes a matrix material such as nylon matrix to provide tear strength.

The polymeric films may be prepared in any convenient sizes.

The biosynthetic polymeric compositions of the invention are exemplified as follows.

TABLE 1

| Ex. | Polyacrylate % 40% Susp. Duramul 609 | Polyacrylate % 50% Susp. Primal ( )E358 | dry weight basis | Glycerol (humectant) % | Protein Gelatin (protein) % | Protein Gum Acacia % | Added Water % | Total Water % | Remarks |
|---|---|---|---|---|---|---|---|---|---|
| 1 | 94.5 | | 37.8 | 2.8 | 0.6 | | 2.1 | 58.8 | A |
| 2 | 92.3 | | 37.1 | 3.5 | 0.9 | | 3.3 | 57.4 | A |
| 3 | 82.5 | | 33.0 | 10.6 | 1.6 | | 5.3 | 54.8 | A |
| 4 | 81.5 | | 32.6 | 3.7 | 3.7 | | 11.1 | 60.0 | B |
| 5 | 78.8 | | 31.5 | 15.2 | 1.5 | | 4.5 | 51.8 | A |
| 6 | 78.5 | | 31.4 | 15.1 | 1.5 | | 4.9 | 52.0 | A |
| 7 | | 61.6 | 30.8 | 7.7 | 7.7 | | 23.1 | 53.8 | C |
| 8 | 72.0 | | 28.8 | 2.5 | | 2.1 | 23.4 | 66.6 | A |
| 9 | 71.3 | | 28.5 | 7.2 | | 7.2 | 14.3 | 57.1 | |
| 10 | 69.3 | | 27.7 | 6.0 | | 5.0 | 19.7 | 61.3 | |
| 11 | 68.8 | | 27.5 | 11.8 | | 9.8 | 9.6 | 50.9 | A |
| 12 | 68.5 | | 27.4 | 5.2 | 5.2 | | 21.1 | 62.0 | C |
| 13 | 68.5 | | 27.4 | 16.8 | | 5.5 | 9.2 | 50.3 | A |
| 14 | 68.3 | | 27.3 | 4.5 | | 9.1 | 18.1 | 59.1 | A |
| 15 | 67.6 | | 27.0 | 12.8 | | 10.5 | 9.1 | 49.7 | |
| 16 | 66.8 | | 26.7 | 13.4 | | 6.7 | 13.1 | 53.2 | A |
| 17 | 66.6 | | 26.6 | 6.7 | 6.7 | | 20.0 | 60.0 | E |
| 18 | 66.0 | | 26.4 | 5.0 | | 4.1 | 24.9 | 64.5 | A |
| 19 | 65.4 | | 26.2 | 20.9 | 3.25 | | 10.45 | 49.65 | A |
| 20 | 63.1 | | 25.2 | 22.0 | | 2.9 | 12.0 | 49.9 | A |
| 21 | 62.5 | | 25.0 | 6.3 | 6.3 | | 25.0 | 62.4 | C |
| 22 | | 48.4 | 24.2 | 10.3 | 10.3 | | 31.0 | 55.2 | C |
| 23 | 60.5 | | 24.2 | 11.3 | | 9.4 | 18.8 | 55.1 | |
| 24 | 59.2 | | 23.7 | 28.4 | 2.8 | | 9.6 | 45.1 | A |
| 25 | 55.6 | | 22.2 | 8.3 | 8.3 | | 27.8 | 61.2 | C |
| 26 | | 43.2 | 21.6 | 11.4 | 11.4 | | 34.0 | 55.6 | C |
| 27 | 51.0 | | 20.4 | 22.0 | | 18.0 | 9.0 | 39.6 | |
| 28 | 46.7 | | 18.7 | 20.1 | | 16.6 | 16.6 | 44.6 | |
| 29 | | 36.6 | 18.3 | 12.7 | 12.7 | | 38.0 | 56.3 | C |
| 30 | 39.1 | | 15.6 | 12.2 | 12.2 | | 36.5 | 60.0 | C |

TABLE 1-continued

| | Polyacrylate % | | | | Protein | | | | |
| | 40% Susp. Duramul 609 | 50% Susp. Primal ( )E358 | dry weight basis | Glycerol (humectant) % | Gelatin (protein) % | Gum Acacia % | Added Water % | Total Water % | |
| Ex. | | | | | | | | | Remarks |
| 31 | 12.3 | | 12.3 | 7.7 | 15.4 | | 46.2 | 64.6 | D,E |
| 32 | | | 7.4 | 7.4 | 18.5 | | 55.6 | 66.7 | F |
| 33 | | | 6.4 | 6.5 | 19.4 | | 58.1 | 67.7 | F |

REMARKS CODE
A Excellent "paint on" - thin film formation
B Good film formation low in protein
C Excellent film formation
D Good film formation high in protein
E Needs warming for use as "paint on"
F Poor film formation
Note:
percentages here and elsewhere are percentages by weight of total composition.

Too high protein content tends to aggregate the emulsified mixture with formation of lumps. A compatible and easily spread emulsion admixture is obtained when the protein content and the humectant concentrations reach about 12% and 15% respectively, and the acrylic copolymer content is approximately 25% by weight.

The compositions of Table 1 are prepared by dissolving the Protein in a minimum amount of hot (80°-95° C.) water (water added) and adding the remainder of the materials.

Films are produced from suitable compositions of Table 1 by the addition of, for example, a nylon matrix. The matrix is placed in a teflon coated tray and a suitable composition applied. The film is then cured in an oven at 85°-95° C. for 20-30 minutes approximately. The resultant films are pliable and elastic and possess good tear strength. The film thickness can be varied from 0.05 to 0.4 m/m.

The films are suitable for protection of first and second degree burns and promote rapid healing.

Compositions suitable as "paint on" formulations remain liquid when stored in the absence of air, for example in air tight bottles. Application of such compositions to minor burns such as sunburn provide immediate relief when applied directly to the affected area.

The compositions may simply be brushed on and dry in about 3 to 5 minutes to a protective polymerised film.

The film provides immediate relief from the symptoms of sunburn and prevent irritation by clothing.

The film is readily removed by soaking in water (or by contacting with water under a shower).

The film absorbs water and sloughs off readily.

Receptor sites for a comparison of Tulle Gras and the biosynthetic films of the invention were prepared along a pigs back by removal of partial thickness (600-700 μm), areas of skin (6×6 cm) using an electric Dermotome. Autografts were used as controls. Zenographs of human skin were also used. Punch biopsies of all areas were studied hystologically three, six, and nine days after the application of the dressings. These films can be sterilized with ethylene oxide, or gamma radiated under which process they can be kept indefinitely. The minimum dose rate is 2.5 Megarad.

THERMAL INJURY OF PORCINE SKIN

To inflict partial and full thickness burns on the back of pigs by change of time and the temperature threshold with a hot water temperature controlled apparatus. The burn area was 6 cm in diameter to produce a round burn patch. BIOSYNTHETIC FILMS were used to cover the burn areas.

TABLE 2

| TEMP. °C. | CONTACT TIME SECONDS | TYPE OF BURN | PUNCH BIOPSIS DAYS 3, 6, 9. |
|---|---|---|---|
| Full thickness burn | | | |
| 80 | 60 | | |
| 80 | 60 | | |
| 80 | 60 | 3° | BIOSYNTHETIC FILM COVER |
| 80 | 120 | | |
| 80 | 120 | | Scar tissue developed when growing together. |
| 80 | 120 | | |
| 80 | 10 | | |
| 80 | 10 | | |
| 80 | 10 | | Scar tissue developed |
| 80 | 15 | | |
| 80 | 15 | | |
| 80 | 20 | | |
| 80 | 20 | | |
| Partial thickness burn | | | |
| 79 | 2.5 | | AFTER 10 DAYS the burned areas recovered to normal under the biosynthetic film cover |
| " | 2.5 | 1° | |
| " | 2.5 | | |
| " | 5.0 | | |
| " | 5.0 | 2° | |
| " | 10.0 | | |
| " | 10.0 | 3° | Scar tissue developed |

TABLE 3

| | PARTIAL THICKNESS RECEPTOR SITES | | |
|---|---|---|---|
| NO. OF PIGS USED | PARTIAL THICKNESS RECEPTOR SITES AREA 6 × 6 cm | PUNCH BIOP- SIES DAYS 3, 6, 9. | HYSTOLOGICAL EXAMINATION |
| 14 | 110 | 9 | COMPLETE RECOVERY OF EPITHELIUM |

In all cases no side reactions occured on donor sites from biosynthetic film cover.

Prior to the experiments all the pigs are anaesthetised.

A first and second degree burn recovered back to normal after a time interval of 12 to 14 days with a biosynthetic film cover and regeneration of the epithilium is complete.

The protein/humectant ratios contained in the acrylic copolymer enables the formed films to be more permeable and capable of absorbing approximately 20% its own weight of water. Such films have been prepared to measure the evaporative process. The films were placed on the upper area and chest on people with normal skin. Weight and temperature changes were measured throughout the experiment. The film thickness was about 300 microns and contained 300 g total solids per square meter.

TABLE 4

TEMPERATURE REDUCTION ON SKIN SURFACE WITH MOISTURE CONTAINED BIOSYNTHETIC FILM

| FILM AREA cm$^2$ | FILM NO. WATER PRESENT T °C. | FILM WITH WATER PRESENT T °C. |
|---|---|---|
| UPPER ARM | | |
| 120 | 34.5 | 30.5 |
| 120 | " | 31.0 |
| 100 | " | 31.0 |
| CHEST | | |
| 225 | " | 31.0 |
| 120 | " | 30.5 |

In all cases temperature measurements were undertaken under the biosynthetic film in close contact with the normal skin. The measurements indicate that a temperature drop of 3.5° C. resulted which is due to the evaporative process of water from the biosynthetic film.

TABLE 5

EVAPORATION LOSS OF WATER FROM BIOSYNTHETIC FILM ON UPPER ARM AND CHEST

| MEASURE-MENT | Wt. OF FILM g. | WATER LOSS % | TIME MIN. | REMARKS |
|---|---|---|---|---|
| 0 | 4.80 | — | — | MALE |
| 1 | 4.31 | 49 | 15 | UPPER ARM |
| 2 | 3.94 | 86 | 30 | AREA |
| 3 | 3.83 | 97 | 45 | 120 cm$^2$ |
| 4 | 3.80 | 100 | 60 | |
| 5 | 3.80 | 100 | 75 | |
| 0 | 4.00 | — | — | FEMALE |
| 1 | 3.60 | 46.5 | 15 | UPPER ARM |
| 2 | 3.40 | 80.0 | 30 | AREA |
| 3 | 3.30 | 94.0 | 45 | 100 cm$^2$ |
| 4 | 3.25 | 100.0 | 60 | |
| 5 | 3.25 | 100.0 | 75 | |
| 0 | 7.60 | — | — | MALE |
| 1 | 7.05 | 45 | 15 | CHEST |
| 2 | 6.90 | 80 | 30 | AREA |
| 3 | 6.80 | 90 | 45 | 225 cm$^2$ |
| 4 | 6.75 | 96.5 | 60 | |
| 5 | 6.75 | 100 | 75 | |

TABLE 6

BIOSYNTHETIC FILM THICKNESS USEFUL FOR BURN APPLICATION

| TOTAL SOLIDS IN FILM g/m$^2$ | FILM THICKNESS MICRONS (APPROX) | WATER ABSORBTION % |
|---|---|---|
| 100 | 180 | 8 |
| 200 | 280 | 15 |
| 300 | 330 | 20 |
| 400 | 400 | 25 |

The most useful biosynthetic films in burn application range from 150–350 microns of thickness. Thinner films suffer from the disadvantage of being fragile and less tear resistant while thicker films are of no value. Experimental evidence suggests that no deterioration occured when these films were placed on arms and legs for a period of 21 days. Dermotological or skin disorders did not occur.

When the formulation is applied with a soft brush to patients who are suffering from acute sunburn (approximate 1° burn) over a large area of the body the pain is considerably lessened.

In the case of other types of burn (Industrial, domestic etc.) paint-on emulsions can be used between fingers, toes and other inaccessible areas where biosynthetic films would not be applicable. During the film forming process the painted areas are being cooled due to the evaporation of water.

The emulsions form a flexible and durable film after five minutes and are about 10–30 microns thick. Such films are permeable and form an air and moisture barrier. The film thickness can, if required, be increased by another paint-on application. Such films, when formed, cannot be easily removed but are highly sensitive to water, for instance, when a painted hand or foot is immersed into water, or a water jet is being directed onto the areas, the film becomes opaque and rolls off on its own accord.

Paint-on formulations can be sterilised by gamma radiation or the incorporation of bacteristats and are useful adjunct to burn treatment.

High gelatine content preparations set solid when reaching room temperature. However by heating such preparations to 35°–40° C. they liquify and are ready for application. Lower gelatine contents remain jelly like and can be used without the warming process.

The biosynthetic films as outlined for burn treatment can be sprayed on one or both sides with a "Siloxane" spray whose silicone molecules polymerise in the air producing a moisture repellent film on contact. The silicone layer is less than one micron in thickness. The film so produced has water and blood repelling properties and can be used for special purposes to prevent adhesion on wounds or materials. This double layer film is permeable to gasses and has all the required characteristics as described in the embodiment of the patent.

FREKOTE 33 and 34, a silicone self-polymerising spray liquid, can be used for the above double layer film preparation as it has very good release and water repellant properties and is non toxic. Double layer films so prepared are sterilised by gamma radiation or the ethylene oxide procedure.

A double layer biosynthetic film with the attachment of a polyurethane sponge 3 m/m thick by means of biomedical pressure adhesive can also be valuable in some burn cases. Blood and moisture is absorbed into the open structure of the polyurethane and excess moisture escapes through the biosynthetic film. Such double layer films can also be used for debridement.

TABLE 7

| BIOSYNTHETIC SEALS DOUBLE LAYER | | |
|---|---|---|
| DURAMUL 617 BIOMEDICAL ADHESIVE EMULSION 40% SOLIDS | | DAVIS FULLER ADHESIVE 3409 EMULSION 40% SOLIDS REMARKS |
| DURAMUL 617 BIOSYNTHETIC FILM ALONE | ADHESIVE 3409 BIOSYNTHETIC FILM ALONE | DIFFICULT TO REMOVE AFTER WATER IMMERSION FOR 5 MINUTES VERY STRONG ADHESION |

TABLE 7-continued

BIOSYNTHETIC SEALS DOUBLE LAYER

| DURAMUL 617 BIOMEDICAL ADHESIVE EMULSION 40% SOLIDS | | DAVIS FULLER ADHESIVE 3409 EMULSION 40% SOLIDS | REMARKS |
| --- | --- | --- | --- |
| TEST 1 | | | |
| GELATINE | %8.3 | 8.3 | STRONG ADHESION FOR BOTH |
| GLYCEROL | %8.3 | 8.3 | BETTER RELEASE WITH 3409 |
| 617 | %83.4 | 83.4 | TREATED FILM WHEN WATER IMMERSED |
| TEST 2 | | | |
| GELATINE | %16.6 | 16.6 | STRONG ADHESION FOR BOTH |
| GLYCEROL | %16.6 | 16.6 | BETTER RELEASE WITH 3409 |
| 617 | %66.8 | 66.8 | TREATED FILM WHEN WATER IMMERSED |
| TEST 3 | | | |
| GELATINE | %18.8 | 18.8 | GOOD ADHESION FOR BOTH |
| GLYCEROL | %18.8 | 18.8 | BETTER RELEASE WITH 3409 |
| 617 | %62.4 | 62.4 | TREATED FILM WHEN WATER IMMERSED |

BIOSYNTHETIC PRESSURE ADHESIVE SEALS FOR BIOSYNTHETIC FILMS

Emulsions with strong adhesion properties are block, or copolymers, of lower molecular weight. These contain polyvinylacetates hydroxyethyleneacrylates emulsifiers, plasticisers and quick tack agents. Such materials are used in the manufacture of pressure adhesive tapes etc. Such emulsions usually contain about 40% solids and when sprayed, or painted onto biosynthetic films have strong properties of adhesion after being heat treated. They can be used with advantage when biosynthetic films with strong adhesion properties are required. However, such emulsions require modification to make them less resistant to water. By incorporation of gelatine and glycerol into the emulsion system the adhesion properties are diminished when coming into contact with water. This is an important property since painless removal is assured when the burn victim is placed in a water bath.

Two such emulsions having similar properties have been tested for this purpose. See Table No. 7.

For test purposes the best release properties were found to be in the Davis Fuller adhesive 3409 which was used in conjunction with a biosynthetic film and placed on an arm and then immersed in luke warm water for five minutes. Test 2 in table 7 indicated the best formulation for the preparation of biosynthetic seals.

The seals are prepared from pressure adhesive treated biosynthetic films which are cut into strips 3 cm in width. These can then be attached to the outer periphery of the biosynthetic films allowing 1.5 cm on the film, and 1.5 cm on the patients skin, to give a complete seal.

Three patients have been treated with biosynthetic polymeric films in the Burn Unit of the Alfred Hospital, Monash University, Melbourne.

In these trials the films were placed on chests and legs. Upon application the films attached themselves to the burned areas or donor sites. The pain threshold was considerably reduced according to patient reaction. As a precautionary measure the films were kept in place by open mesh bandages. The films used were approximately 30×25 cm in size allowing for a continuous and larger area to be covered than is normal with interrupted layers of pig skin. This resulted in non epithelium regeneration free from scar tissue. No detrimental side effect, or adverse skin reactions could be observed on the treated areas. Upon removal the films were still pliable and soft and ingress of bacteria had been halted. It therefore appears that biosynthetic polymeric films function in a similar way to pig skin preparations, and even have certain advantages.

It also appears that in addition to burn dressings these films can be used in cosmetic surgery and all other external wounds.

CONCLUSIONS

On pigs biosynthetic polymer films are as effective as Tulle Gras in promoting epithelialization. Unlike Tulle Gras these films minimize bleeding and remain pliable, and are premeable to gasses and vapours. In addition they are transparent so that wound healing may be observed without the trauma to the patient of painful removal. However, should the films stick to the blood, they can be easily removed by application of warm water, or immersion in a bath. It has been demonstrated experimentally that the biosynthetic polymer films stop ingress of bacteria.

Biosynthetic polymer films are quick and easy to reproduce and do away with the labour intensive and unpleasant process of killing the pigs and subsequently cleaning and removing their skins, followed by the expensive method of storage under liquid nitrogen.

It will therefore be clearly seen that, in every respect, the use of biosynthetic films will bring about a considerable economy in the treatment of burn patients.

It has also been found that when a composition of the invention when painted or applied in liquid form to a burn, such as obtained by over-exposure to the sun, a film forms on the skin which provides remarkable relief from the symptoms of sunburn and enables rapid recovery of the burnt skin beneath the biosynthetic polymeric film so formed.

I claim:

1. A biosynthetic polymeric composition adapted to form a vapor permeable film, said composition including: (a) 10% to 40% by weight of a water dispersible acrylic polymer containing from 50 to 500 monomeric units; (b) 2% to 30% by weight of a humectant selected from the group consisting of glycerol, polyethylene glycol, and propyl 1, 2 diol; (c) 0.5% to 20% by weight of a material selected from a group consisting of gelatin, gum acacia, and albumin; and (d) 30% to 87.5% by weight water.

2. A method of producing a vapor permeable biosynthetic polymeric film for use as a wound dressing said method comprising: (a) preparing a composition consisting of: (i) 10% to 40% by weight of a water dispersible acrylic polymer containing from 50 to 500 monomeric units; (ii) 2% to 30% by weight of a humectant selected from the group consisting of glycerol, polyethylene glycol, and propyl 1, 2 diol; (iii) 0.5% to 20% by weight of a material selected from a group consisting of gelatin, gum acacia, and albumin; and (iv) 30% to 87.5% by weight water; and (b) pouring said composition into a liquid film and allowing said film to polymerize and harden.

3. A method according to claim 2 which further comprises dispersing in said liquid film a strengthening mesh matrix to increase the strength of said film.

4. A method of producing a vapor permeable biosynthetic polymeric film for use as a wound dressing, said method comprising the application to a wound of a composition including; (a) 10% to 40% by weight of a water dispersable acrylic polymer containing from 50 to 500 monomeric units; (b) 2% to 30% by weight of a humectant selected from the group consisting of glycerol, polyethylene glycol, and propyl 1, 2 diol; (c) 0.5% to 20% by weight of a material selected from a group consisting of gelatin, gum acacia, and albumin; and (d) 30 to 87.5% by weight water and allowing said composition to polymerize and harden.

5. A method according to claim 4 wherein said application comprises brushing said composition on said wound.

6. A method according to claim 4 wherein said application comprises spraying said composition on said wound.

7. A method according to claim 5 or 6 wherein said wound is a burn up to and including the second degree.

* * * * *